(12) United States Patent
Suter et al.

(10) Patent No.: US 12,407,660 B2
(45) Date of Patent: *Sep. 2, 2025

(54) METHODS AND SYSTEMS FOR PROCESSING DATA OF AN ANALYTICAL INSTRUMENT FOR ANALYZING BIOLOGICAL SAMPLES

(71) Applicant: Roche Diagnostics Operations, Inc., Indianapolis, IN (US)

(72) Inventors: Urs Suter, Zurich (CH); Alejandro Morcillo Montejo, Barcelona (ES); Antonio Tienda Fernandez, Barcelona (ES); Stephen Martin, Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/353,378

(22) Filed: Jul. 17, 2023

(65) Prior Publication Data

US 2023/0362146 A1 Nov. 9, 2023

Related U.S. Application Data

(63) Continuation of application No. 17/151,950, filed on Jan. 19, 2021, now Pat. No. 11,743,239, which is a
(Continued)

(30) Foreign Application Priority Data

May 18, 2017 (EP) .................................... 17382283

(51) Int. Cl.
*H04L 9/40* (2022.01)
*A61B 5/00* (2006.01)
(Continued)

(52) U.S. Cl.
CPC ........ *H04L 63/0478* (2013.01); *A61B 5/0022* (2013.01); *G16H 10/60* (2018.01);
(Continued)

(58) Field of Classification Search
CPC ............... H04L 63/0442; H04L 9/0825; H04L 9/0866; H04L 9/14; H04L 9/30
See application file for complete search history.

(56) References Cited

U.S. PATENT DOCUMENTS 6,128,735 A 10/2000 Goldstein et al.
8,412,926 B1 4/2013 Gerraty
(Continued)

FOREIGN PATENT DOCUMENTS

CN 101436208 A 5/2009
CN 103561024 A 2/2014
(Continued)

OTHER PUBLICATIONS

European Search Report issued Aug. 7, 2017, in Application No. EP 17382283, 8 pp.

*Primary Examiner* — Beemnet W Dada
(74) *Attorney, Agent, or Firm* — Lee & Hayes, P.C.

(57) ABSTRACT

A method for processing data of an analytical instrument for analyzing biological samples is presented. The method comprises receiving instrument data from the analytical instrument at a data processing module communicatively connected with the analytical instrument, generating metadata from the received instrument data at the data processing module, applying a first encryption to the instrument data at the data processing module, applying a second encryption to the generated metadata at the data processing module, and transmitting the encrypted metadata and encrypted instrument data to a remote server. The remote server and the data processing module are communicatively connected. The
(Continued)

method also comprises removing the second encryption from the metadata at the remote server and forwarding the instrument data encrypted by the first encryption from the remote server to a management system of the analytical instrument.

20 Claims, 4 Drawing Sheets

Related U.S. Application Data continuation of application No. 15/971,048, filed on May 4, 2018, now Pat. No. 10,938,793.

(51) Int. Cl.
*G16H 10/60* (2018.01)
*G16H 40/20* (2018.01)
*G16H 40/67* (2018.01)
*H04L 9/08* (2006.01)
*H04L 9/14* (2006.01)
*H04L 9/30* (2006.01)
*H04L 67/561* (2022.01)
*H04L 67/565* (2022.01)
*H04W 12/033* (2021.01)
*G06F 21/62* (2013.01)
*H04L 69/08* (2022.01)

(52) U.S. Cl.
CPC ............ *G16H 40/20* (2018.01); *G16H 40/67* (2018.01); *H04L 9/0825* (2013.01); *H04L 9/0866* (2013.01); *H04L 9/14* (2013.01); *H04L 9/30* (2013.01); *H04L 63/0442* (2013.01); *H04L 67/561* (2022.05); *H04L 67/565* (2022.05); *H04W 12/033* (2021.01); *A61B 5/00* (2013.01); *G06F 21/6245* (2013.01); *H04L 63/0471* (2013.01); *H04L 69/08* (2013.01)

(56) References Cited

U.S. PATENT DOCUMENTS

| | | |
|---|---|---|
| 2001/0027331 A1 | 10/2001 | Thompson |
| 2003/0235308 A1 | 12/2003 | Boynton et al. |
| 2007/0079117 A1 | 4/2007 | Bhogal et al. |
| 2007/0124471 A1 | 5/2007 | Harada et al. |
| 2008/0021834 A1 | 1/2008 | Holla et al. |
| 2010/0257351 A1 | 10/2010 | O'Connor et al. |
| 2011/0314088 A1 | 12/2011 | Matzkel et al. |
| 2012/0254474 A1 | 10/2012 | Brown et al. |
| 2012/0260089 A1 | 10/2012 | Gupta et al. |
| 2013/0067031 A1 | 3/2013 | Shedrinsky |
| 2014/0177825 A1 | 6/2014 | Mattsson et al. |
| 2015/0052358 A1 | 2/2015 | Udupi et al. |
| 2016/0308842 A1 | 10/2016 | Choe et al. |
| 2017/0041366 A1 | 2/2017 | Dowlatkhah et al. |
| 2017/0124257 A1 | 5/2017 | Dowlatkhah et al. |

FOREIGN PATENT DOCUMENTS

| | | | | |
|---|---|---|---|---|
| DE | 10041514 C2 | | 3/2003 | |
| EP | 2863332 A1 | * | 4/2015 | ............ G06F 21/62 |
| JP | 2003-005645 A | | 1/2003 | |
| JP | 2006244425 A | | 9/2006 | |
| JP | 2015-233173 A | | 12/2015 | |
| WO | 2013/109517 A1 | | 7/2013 | |
| WO | 2014/033568 A1 | | 3/2014 | |
| WO | 2015/055738 A1 | | 4/2015 | |

* cited by examiner

METHODS AND SYSTEMS FOR PROCESSING DATA OF AN ANALYTICAL INSTRUMENT FOR ANALYZING BIOLOGICAL SAMPLES

CROSS-REFERENCE TO RELATED APPLICATIONS

This application is a continuation of U.S. application Ser. No. 17/151,950, filed Jan. 19, 2021, now allowed, which is a continuation of U.S. application Ser. No. 15/971,048, filed May 4, 2018, now issued, which claims the benefit of EP 17382283.4, filed May 18, 2017, the disclosures of which are hereby incorporated by reference in their entirety.

BACKGROUND

The present disclosure generally relates to methods and systems for processing data of an analytical instrument for analyzing biological samples and, in particular, to methods and systems for encrypted transmission of data.

Many prior art analytical instruments (such as automated analyzers) have been designed as stand-alone devices or devices operating in a closed and controlled network environment with heavily restricted access. For instance, networks in which some prior art analytical instruments operate can be limited to a single cable connection between the respective analytical instrument and a control device. Moreover, analytical instruments often times stay employed in the field for a comparatively extended period of time.

As a result, legacy instruments with no, or limited, communication capabilities can be found relatively frequently. This might be even more the case for analytical instruments deployed in general practitioners' offices, pharmacies or in patients' homes.

Now, it is desirable in many situations to integrate these analytical instruments in more extended computer networks (e.g., a hospital network spanning multiple sites).

In addition, it might be desirable to allow third parties to be included in the network to provide different services to operators of the analytical instruments (e.g., third parties not included in a secure environment of a hospital or a general practitioner's office). For instance, a vendor of an analytical instrument might want provide different analysis and maintenance services for its analytical instruments deployed at a remote site.

Networking analytical instruments (in particular legacy instruments) and transmitting data provided by analytical instruments can be challenging, in particular from a data security perspective.

SUMMARY

According to the present disclosure, a system and method for processing data of an analytical instrument for analyzing biological samples. The method can comprise receiving instrument data from the analytical instrument at a data processing module communicatively connected with the analytical instrument, generating metadata from the received instrument data at the data processing module, applying a first encryption to the instrument data at the data processing module, applying a second encryption to the generated metadata at the data processing module, and transmitting the encrypted metadata and encrypted instrument data to a remote server. The remote server and the data processing module are communicatively connected. The method can also comprise removing the second encryption from the metadata at the remote server and forwarding the instrument data encrypted by the first encryption from the remote server to a management system of the analytical instrument.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
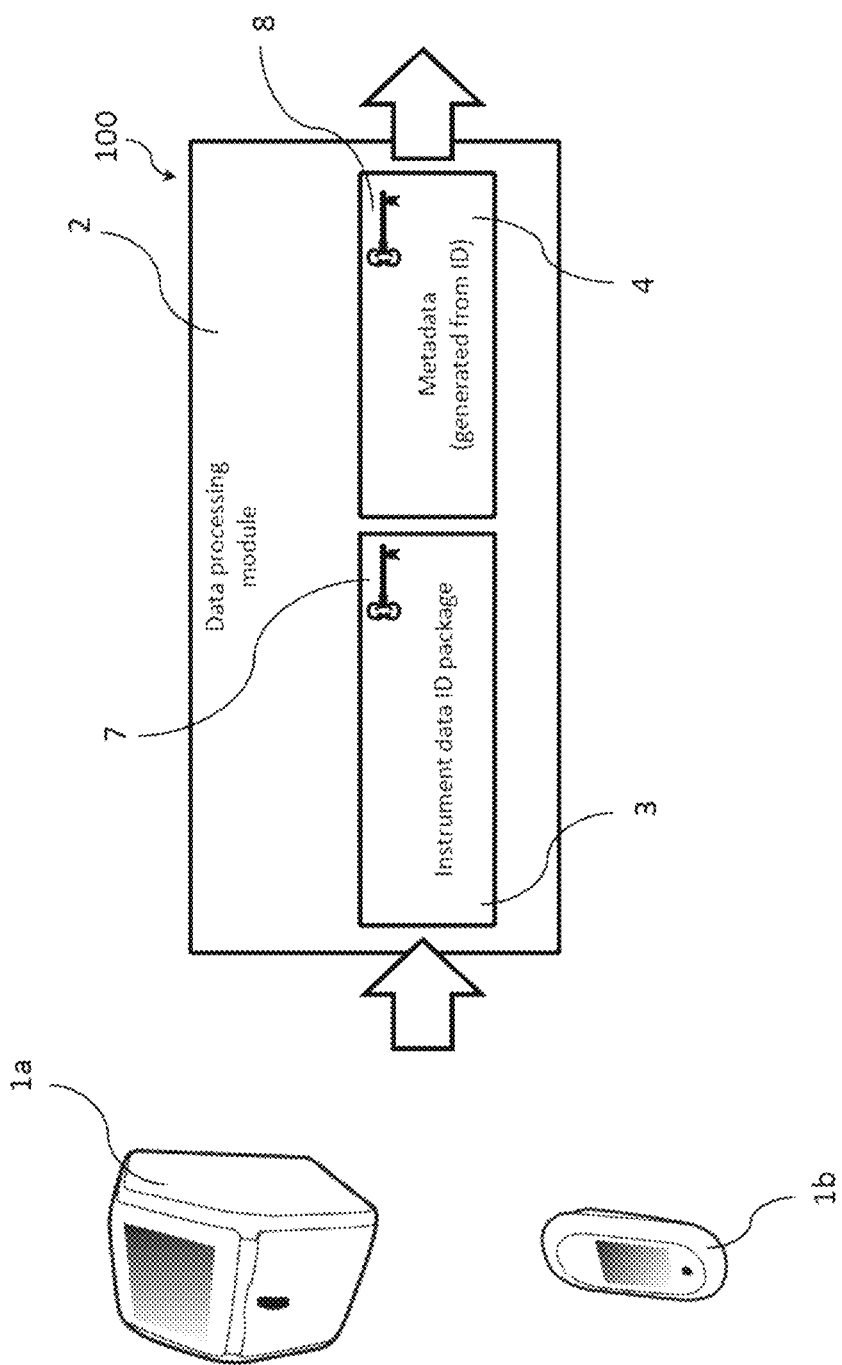
FIG. 1 illustrates a schematic diagram of a data processing module according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for processing data of an analytical instrument for analyzing biological samples is presented. The method can include receiving instrument data from the analytical instrument at a data processing module communicatively connected with the analytical instrument, generating metadata from the received instrument data at the data processing module, applying a first encryption to the instrument data at the data processing module, applying a second encryption to the generated metadata at the data processing module and transmitting the encrypted metadata and encrypted instrument data to a remote server. The remote server and the data processing module are communicatively connected. The method can also comprise removing the second encryption from the metadata at the remote server and forwarding the instrument data encrypted by the first encryption from the remote server to a management system of the analytical instrument.

A method for processing data of a management system of analytical instruments is also presented. The method can include receiving input data at the management system of analytical instruments, generating metadata based on the input data at the management system of analytical instruments, applying a first encryption to the input data at the management system, applying a second encryption to the generated metadata at the management system and transmitting the encrypted data from the management system to a remote server. The remote server and the management system are communicatively connected. The method can also comprise removing the second encryption from the data at the remote server, transmitting the input data to a data processing module communicatively connected to an analytical instrument for analyzing biological samples, removing the first encryption from the input data at the data processing module, and forwarding the input data from the data processing module to the analytical instrument.

A system can be configured to carry out the above methods.

Particular embodiments can be implemented so as to realize one or more of the following advantages.

Firstly, the techniques of the present disclosure can be used to secure that data which may not be accessible outside of a secure network (e.g., data identifying a patient in a hospital or laboratory network), can be communicated towards and from a management system even if third party devices are included in the data transmission part. In this manner, the techniques can improve data security in networks including different third party network devices.

Secondly, third parties can be granted access to particular data (e.g., metadata without sensitive patient data) for providing services from outside a secure network (e.g., a hospital or laboratory network). This can be helpful, e.g., to provide maintenance and quality control services as well as analytics services for analytical instruments. For example, it might be possible to analyze or predict a state of analytical instrument based on metadata, or to analyze the metadata to provide the operators of an analytical instrument with additional information. In addition, or alternatively, computing-power intensive operations can be off-loaded to remote servers. The techniques of the present disclosure can ensure that data security can be maintained while allowing these and other actions involving third parties.

Thirdly, the techniques of the present disclosure can be used to set up a network including one or more analytical instruments, a remote server (e.g., a server of a vendor of the analytical instrument), and a management system of analytical instruments (e.g., a main hospital data center) in an efficient manner. In particular, the data processing module can provide networking capabilities for analytical instruments which might not otherwise be capable of being integrated in such networks (e.g., legacy analytical instruments having no or only limited connectivity). For example, the data processing module can be provided with drivers necessary to process data received from the analytical instruments and to enforce a predetermined data security policy.

The term 'analytical instrument' as used herein can refer to any kind of technical device for use in laboratory work, e.g., in the clinical, chemical, biological, immunology or pharmaceutical area or the like used for performing a test or measurement on a biological sample in-vitro or in-vivo.

'Analytical instruments' may not necessarily be located in a dedicated laboratory. Rather, the term can also include stand-alone instruments for carrying out analytic procedures, e.g., in the clinical, chemical, biological, immunology or pharmaceutical area. For example, a benchtop device in point-of-care settings such as physician clinics or pharmacies or devices for home-use can also be analytical instruments according to the present disclosure. In other examples, analytical instruments can be employed in ambulatory and emergency settings (e.g., in case of an outbreak of an epidemic disease). For instance, an analytical instrument can be present in an ambulance.

Several possible aspects and implementations of analytical instruments will be discussed in the following paragraphs.

Examples of such analytical instruments are clinical chemistry analyzers, coagulation chemistry analyzers, immunochemistry analyzers, hematology analyzers, urine analyzers, nucleic acid analyzers, used to detect the result of chemical or biological reactions or to monitor the progress of chemical or biological reactions.

Analytical instruments may comprise components to perform fluid transfer and dosing, fluid homogenization (mixing), temperature control, and measurements of chemical or physical parameters. For example, the devices can include fluid dispensing components (e.g., a pipettor or a valve), a stirrer, a tempering device, a shaker, and/or an agitator.

An analytical instrument may comprise units assisting with the pipetting, dosing, and mixing of samples and/or reagents. The analytical instrument may comprise a reagent-holding unit for holding reagents to perform assays (in particular for performing a confirmation test). Reagents may be arranged, e.g., in the form of containers or cassettes containing individual reagents or group of reagents, placed in appropriate receptacles or positions within a storage compartment or conveyor. It may comprise a consumable feeding unit. The analytical instrument may comprise a process and detection system whose workflow is optimized for certain types of analysis.

In other examples, analytical instrument can include an analysis system or a work-cell of an analysis system or analyzer.

'Analytical instruments' as used herein can also comprise a control unit, or a controller, operatively coupled to control the operations of the analytical instrument. In addition, the controller may be operable to evaluate and/or process gathered analysis data, to control the loading, storing and/or unloading of samples to and/or from any one of the analytical instruments, to initialize an analysis or hardware or software operations of the analytical instrument used for preparing the samples, sample tubes or reagents for said analysis and the like.

An analytical instrument can be an analyzer for analyzing a mechanical, optical, chemical or biological property of a sample.

An analytical instrument can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer comprises, without limitation, concentrations of the analyte in the sample, a digital (e.g., yes or no, or positive or negative) result indicating the existence of the analyte in the sample (corresponding to a concentration above the detection level), optical parameters, images, cell or particle counts, DNA or RNA sequences, data obtained from mass spectrometry of proteins or metabolites and physical, mechanical, optical, electrical or chemical parameters of various types.

Analytical instruments can have different sizes. In one example, an analytical instrument can be a handheld device. In other examples, an analytical instrument can be bench-top device. In still other examples, an analytical instrument can be a multi-stage automated analyzer.

The analytical instruments can be automated or semi-automatic in some examples. However, in other examples the analytical instruments can be configured so that some or all steps of an analysis process are carried out manually.

In general, the analytical instruments in the present disclosure can have the capability to communicate over at least one communication channel (e.g., using the communication networks discussed below).

The term 'biological sample' or 'sample' refers to material(s) that can potentially contain an analyte of interest. The sample can be derived from a biological source, such as a physiological fluid, including whole blood, plasma, serum, saliva, ocular lens fluid, cerebrospinal fluid, sweat, urine, stool, semen, milk, ascites fluid, mucous, synovial fluid, peritoneal fluid, amniotic fluid, tissue, cells, or the like. The biological sample can be pretreated prior to use. Pretreatment can involve centrifugation, filtration, dilution, concentration and/or separation of sample components including analytes of interest, inactivation of interfering components, and the addition of reagents.

A sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid.

A sample can be treated before analytical testing is done. Blood sampled from a patient can, e.g., be centrifuged to obtain serum or treated with anti-coagulants to obtain plasma. However, the techniques of the present disclosure may not be limited to blood samples or samples derived from blood. In other examples, other biological samples can be used to perform confirmation tests (as long as the techniques of the present disclosure can be applied to detect a presence of the respective analyte).

The term 'analyte' as used in the present disclosure can refer to a substance or constituent that is of interest in an analytical procedure.

A 'control unit' or 'controller' can control analytical instrument in a way that the necessary steps for the processing protocols can be conducted by the analytical instrument. That can mean the controller may, for example, instruct an analytical instrument to conduct certain pipetting steps to mix the liquid biological sample with reagents, or the controller can control the analytical instrument to incubate the sample mixtures for a certain time etc. The control unit may receive information from a data management unit regarding which steps need to be performed with a certain sample. In some embodiments, the controller might be integral with the data management unit or may be embodied by a common hardware. The controller may, for instance, be embodied as a programmable logic controller running a computer-readable program provided with instructions to perform operations in accordance with a process operation plan. The controller may comprise a processor and a memory. The controller may be set up to control, for example, any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of a light source, e.g. selection of the wavelength, or the like. In particular, the controller may include a scheduler, for executing a sequence of steps within a predefined cycle time. The controller may further determine the order of samples to be processed according to the assay type, urgency, and the like.

The term 'communication network' as used herein can encompass any type of wireless network, such as a WIFI, GSM, UMTS, LTE or other wireless network or a cable based network, such as Ethernet or the like. In particular, the communication network can implement the Internet protocol (IP). However, in other examples a communication network can implement a proprietary communication protocol. In some example, the communication network can comprise a combination of cable-based and wireless networks.

The term 'metadata' in the present disclosure can refer to any type of data generated from or based on instrument data from an analytical instrument. The data generation process can, e.g., include selecting of data items of the instrument data, modifying data items of the instrument, combining data items of the instrument data or other processing steps. Further details regarding possible features of metadata will be explained below. In any case, 'metadata' can include data items of the instrument data (i.e., the term 'metadata' not exclusively relates to data items not contained in the instrument data). However, metadata cannot include all data items of the instrument data it is generated from (i.e., it cannot be identical to the instrument data).

Unless specified otherwise, the terms 'about', 'substantially' and 'approximately' as used herein can refer to a deviation of +/−10% of the indicated value. If two values are 'substantially' or 'approximately' equal, this can mean that the values differ by at most 10% (determined starting from the smaller value).

General Operations of the Data Processing Module

FIG. 1 includes a schematic diagram illustrating a data processing module 2 according to the present disclosure. In the example of FIG. 1, two analytical instruments 1*a*, 1*b* (e.g., a handheld device 1*b* and an automated in-vitro analyzer 1*a*) can provide instrument data 3 (abbreviated as "ID" in some passages of the description and the drawings) to a data processing module 2 as will be described below.

The data processing module 2 can be configured in many different ways.

In one example, the data processing module 2 can be a stand-alone hardware module configured to be connected to an analytical instrument 1*a*, 1*b* (e.g., through a communication network or through a direct cable or wireless connection).

The stand-alone hardware module can include a housing 100 encompassing all components required in the data processing module 2. In some examples, the data processing module 2 can be a stand-alone hardware module having a form-factor of less than 20 cm×20 cm×20 cm (length×height×width).

For instance, the data processing module 2 might have a form-factor of a box (e.g., similar to a WIFI router) adapted to be connected to the analytical instrument 1*a*,1*b* through a data communication port (wired or wireless) of the analytical instrument 1*a*,1*b*.

In other examples, the data processing module 2 can be a plug-in hardware module configured to be inserted inside a housing of a different device. In one example, the plug-in hardware module can be adapted to be arranged in the analytical instrument 1*a*, 1*b* or another device connected to the analytical instrument 1*a*, 1*b* (e.g., in the form of a slide-in module). The plug-in module can then be communicatively coupled to the analytical instrument 1*a*, 1*b* through an interface of the analytical instrument 1*a*, 1*b* (e.g., an external communication port or an internal interface).

The data processing module 2 can be equipped with different functional units besides the functional units required to perform the operations described herein. In some examples, the data processing module 2 can include a dedicated power supply. For instance, the data processing module 2 can include one or more batteries or capacitors to provide power for the different functions of the data processing module 2.

In addition, or alternatively, the data processing module 2 can include a transceiver to provide wired or wireless communication capabilities. In one example, the data processing module 2 can be configured to communicate over a wired or wireless public telephone network. In addition, or alternatively, the data processing module 2 can be configured to establish a wire-based or wireless internet connection.

In the examples above, the data processing module 2 can be configured as a single hardware unit. However, in other examples, the data processing module 2 can be embodied as multiple hardware units (e.g., a main body and an antenna unit).

In still other examples, the data processing module 2 can be configured as a software module.

For instance, the data processing module 2 might be a software module residing on a remote server or at least being controlled from a remote server. In some examples, the data processing module 2 can be configured to operate as infrastructure as a service ("IaaS") or software as a service ("SaaS").

In still other examples, the data processing module 2 can be provided by a mixture of hardware and software modules (e.g., a hardware module using a software module running on a remote server).

Regardless of the particular configuration (e.g., hardware or software), the data processing module 2 can be configured to carry out the techniques for processing data of an analytical instrument 1a, 1b for analyzing biological samples according to the present disclosure.

In the present disclosure, we will distinguish between instrument data 3 provided by the analytical instrument 1a, 1b and metadata 4 which can be data generated based on the instrument data 3. Instrument data 3 can include any data generated by analytical instruments 1a, 1b (e.g., data generated by any one of the analytical instruments discussed above). In general, instrument data 3 can include any data produced by an instrument during normal operation (e.g., while carrying out tests on samples), setup, maintenance or during other modes of operation of the analytical instrument.

In one example, the instrument data 3 can include data relating to a measurement or test performed by the analytical instrument 1a, 1b or with the analytical instrument 1a, 1b. In other examples, the instrument data 3 can include data relating to a status of the analytical instrument 1a, 1b (e.g., data produced by sensors monitoring the analytical instrument). In still other examples, the instrument data 3 can include data relating the environment of the analytical instrument 1a,1b gathered by the analytical instrument 1a, 1b (e.g., data generated by sensors in the analytical instrument such as temperature or humidity data).

In general, instrument data 3 can include two types of data—a first type of data and a second type of data. The first type of data can include information which may not be accessible to parties outside a predetermined secure network environment the analytical instrument resides in (e.g., a hospital, laboratory or pharmacy network or the network of a doctor's office).

The second type of data can be data that does not include information described above. This data might be made accessible to parties outside the predetermined secure network environment. In the present disclosure, the first type of data will also be referred to a "sensitive data" or "confidential data". Accordingly, the second type of data will be referred to as "non-sensitive data" or "non-confidential data" in the present disclosure.

The first type of data can include patient data which might be suitable to identify a particular patient (e.g., name, address, date of birth or other data items that might be suitable to identify a particular patient). In addition, or alternatively, the first type of data can include private patient data (e.g., data relating to anamnesis, test results or a group of test results and other private data). These two types of data (i.e., patient specific data and private data of patients) can also be referred to in the present disclosure as "patient-specific data." Whether a data item falls within one of these classes or not might be determined by law or by other regulations.

In addition, or alternatively, the first type of data can include data which can be suitable to identify a particular entity where the respective analytical instrument is located (e.g., data identifying a hospital, laboratory or doctor's office). In addition, or alternatively, the first type of data can include private data of an organization operating the respective analytical instrument 1a, 1b (e.g., billing data or data identifying an operator of the analytical instrument 1a,1b). These two types of data (i.e., specific data and private data of entities operating the analytical instrument 1a, 1b) can also be referred to in the present disclosure as "client-specific data."

On the other hand, the second type of data can be any data which does not have the above referenced properties. For example, the second type of data can include data that is not suitable to identify a particular patient (e.g., year of birth, post code, city of residence or other data which is not suitable to identify a particular patient).

As can be seen in FIG. 1, the data processing module 2 can also process metadata 4 generated from the instrument data 3. In general, the metadata 4 can include data generated from or based on the instrument 3 data from an analytical instrument. For instance, metadata 4 can be the second type of data discussed above.

The generation process of metadata 4 can include one or more of the following process steps. In one example, the metadata 4 can be a sub-selection of data items contained in the instrument data 3. For instance, the metadata generation process can include selecting one or more data items contained in the instrument data 3. For instance, measurement or test data can be selected from a data set including measurement or test data and data identifying a patient for which the respective test or measurement was performed.

In these examples, the metadata 4 can include data items identically contained in the instrument data 3 (so that the metadata generation process can also be seen as a filtering operation of the instrument data).

In other examples, the metadata 4 can be a sub-selection of data items contained in the instrument data 3 which can be further processed. For example, a data item in the instrument data 3 can include a birthday of a patient which can then be processed to yield only the year of birth as metadata 4. In another example, the instrument data 3 might include a measurement value for a particular test. Processing of this data might include classifying the measurement value in one of several classes (e.g., "normal," "low," or "high"). The metadata 4 can then only include the class the measurement value falls in.

In still other examples, the metadata 4 can be generated based on data items contained in the instrument data 3 and further data. For example, the metadata 4 can be generated based on data for different patients or from different analytical instruments, or both.

In one example, the metadata generating process can include removal of all data of the first type of data discussed above. For example, the generation of metadata 4 can include removal of patient-specific or client-specific data received from the analytical instrument 1a,1b.

In the following sections, we will sometimes refer to "generation" of metadata 4 and sometimes to "selection" of metadata 4. As can be seen from the explanation above, both terms can refer to extracting data from the instrument data 3, with or without additional processing steps.

In general, the data processing module 2 can apply different types of encryption on the instrument data 3 and the metadata 4 (in the present disclosure, the expressions "applying an encryption to data" and "encrypting data" can be used synonymously).

A first encryption 7 can be applied to the instrument data 3 and a second encryption 8 can be applied to the metadata 4. In the present disclosure, it can sometimes also refer to a "first level of encryption" when speaking of the "first encryption" and, respectively, to a "second level of encryption" when discussing the "second encryption." These expressions can be used synonymously.

The first and second encryption 7, 8 can be different. This can mean that an entity or device capable of decrypting data encrypted with one of the encryptions by particular means (e.g., using a particular key) cannot encrypt data encrypted with the respective other encryption by the same means.

In general, the metadata 4 may not be encrypted with the first encryption 7. In the example of FIG. 1, the metadata 4 may likewise not be encrypted with the second encryption 8. However, in other examples, both the instrument data 3 and the metadata 4 can be encrypted with the second encryption 8.

The first encryption 7 and the second encryption 8 can be any encryption suitable to encrypt electronic data. Example encryption techniques that can be used to generate the first and second encryption 7, 8 will be discussed below in connection with FIG. 2.

In addition to the metadata generation process and the encryption process, the data processing module 2 can be configured to transmit the encrypted data over a communication network (not shown in FIG. 1). The communication network can be any wired or wireless communication network (e.g., any one of the communication networks discussed above). The transmitted data can then be further processed at a remote location. This operation will now be discussed in more detail in connection with FIG. 2.

Network Including Data Processing Module

Figure 2:
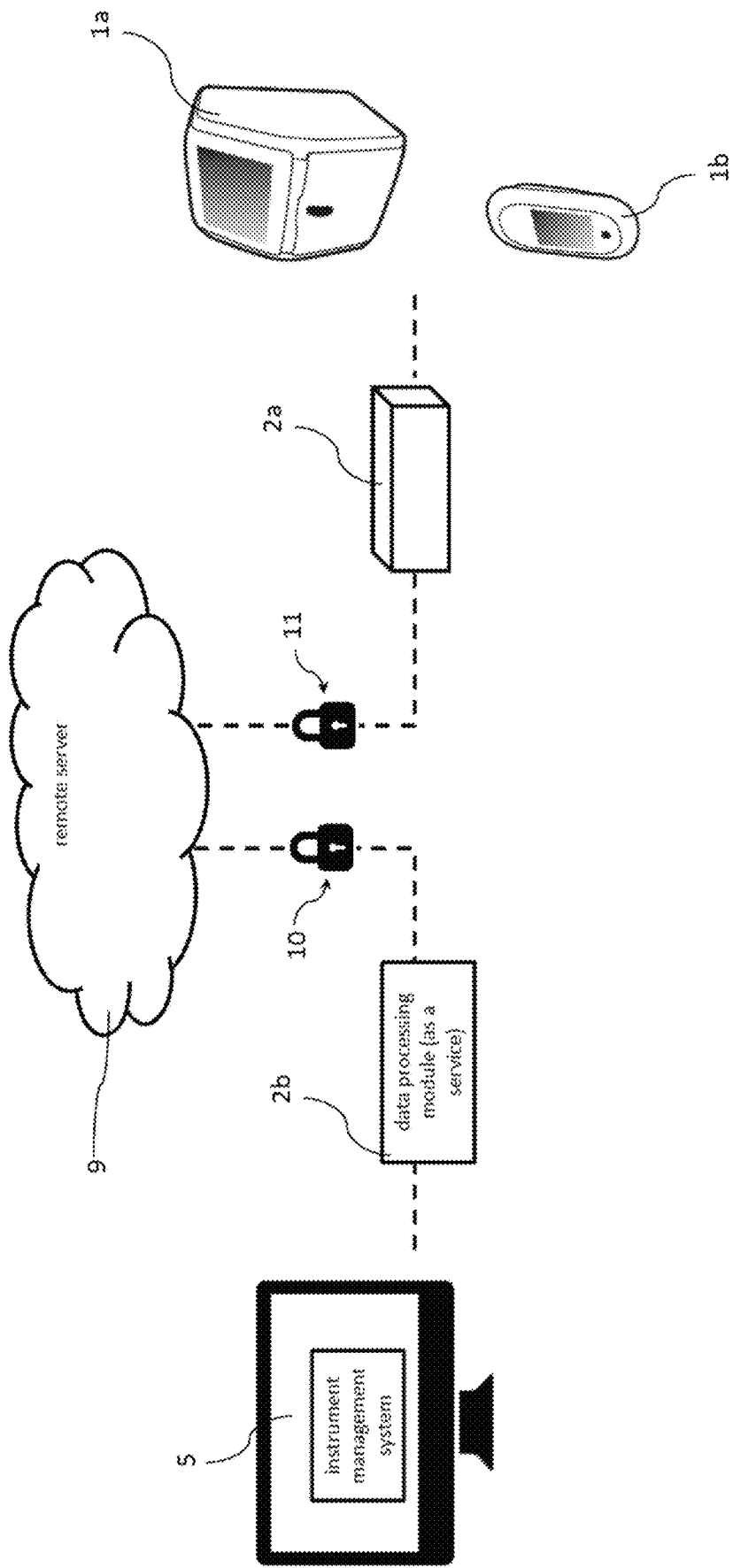
FIG. 2 illustrates a schematic diagram including a network set up by using a data processing module according to an embodiment of the present disclosure.

FIG. 2 shows two data processing modules 2a, 2b in a network environment. Similar to FIG. 1, FIG. 2 shows analytical instruments 1a, 1b coupled to a data processing module 2a. In some examples, a particular data processing module can be connected only to a single analytical instrument to serve this single analytical instrument. In other examples, a data processing module can be coupled with a plurality of analytical instruments and serve each of these instruments. The data processing module can be statically or dynamically assigned to analytical instruments.

In the example of FIG. 2, the data processing module 2a can be a stand-alone hardware module. However, in other examples, the data processing module 2a can be any of the data processing modules 2 discussed above in connection with FIG. 1.

As described, the data processing module 2a receives instrument data 3 from an analytical instrument 1a, 1b and processes this data using the above described techniques. The so-processed data 11 is then transmitted to a remote server 9. As depicted in FIG. 2, the data 11 can be encrypted. In some examples, the data 11 can include instrument data 3 encrypted with a first encryption 7 and metadata 4 encrypted with a second encryption 8 (e.g., both types of data are "single encrypted"). In other examples, the data 11 can include instrument data 3 encrypted with a first encryption 7 and a second encryption 8 and metadata 4 encrypted only with a second encryption 8 (e.g., the instrument data 3 is "double encrypted" and the metadata 4 is "single encrypted").

The data processing module 2a can be connected to the remote server 9 through any direct or indirect network connection. In one example, the data processing module 2a can be connected to the internet to establish a connection to the remote server 9.

The remote server 9 can be a server run by a vendor of the analytical instrument(s) 1a, 1b in some examples. However, in other examples the remote server 9 can be a server run by a different third party operator (e.g., a provider of analytical services for the entity operating the analytical instruments 1a, 1b). The remote server 9 might be located outside a secure network of the entity operating the analytical instrument(s) 1a, 1b in some examples.

The further processing steps of the data will be discussed. At the remote server 9, the second encryption 8 can be removed. As a result, the metadata 4 can be accessed and processed at the remote server 9. Examples of how the metadata 4 can be processed at the remote server 9 will be discussed below in connection with FIG. 3 and FIG. 4. However, in some examples, the remote server 9 can only remove the second encryption 8 and does not process the metadata 4.

Regardless of the processing steps performed by the remote server 9 on the data 11, the remote server 9 can forward instrument data 10 encrypted by the first encryption 7 to a management system 5 of the analytical instrument 1a, 1b for analyzing biological samples.

For example, the management system 5 of the analytical instrument 1a, 1b for analyzing biological samples can be a data center of an operator of the analytical instrument(s) 1a, 1b. As described above, the operator of the analytical instrument 1a, 1b can be a hospital, a pharmacy, a laboratory, a doctor's office or another entity. Accordingly, the instrument management system 5 can be a hospital management system, a pharmacy management system, a management system of a doctor's office or laboratory or of another entity. In some examples, the instrument management system 5 can be part of a laboratory information system ("LIS") or a hospital information system ("HIS").

It can be pointed out that the instrument management system 5 can take a variety of different forms. For instance, in a medical practice the instrument management system 5 can be a data processing system residing on a personal computer or a local server. In other examples, the instrument management system 5 can be a management system of a large entity such as a hospital network including many sites.

In some examples, the instrument management system 5 can be local to the analytical instrument 1a, 1b. In other examples, the instrument management system 5 can be a remote instrument management system.

In other words, the analytical instruments 1a, 1b connected to the instrument management system 5 through the data processing module 2a, 2b can be arbitrary located. In one example, the analytical instrument 1a, 1b can be located in a patient's home or can be non-stationary (e.g., in an ambulance) and can be connected to the instrument management system 5 through the data processing module 2a.

At the instrument management system 5, the first encryption 7 can be removed and the instrument data 3 can be processed. In this manner, the data processing module 2a can allow for a secure transmission of data from the analytical instruments 1a, 1b to the data processing module 2a via the remote server 9. In particular, an operator of the remote server 9 does not get access to sensitive patient or client data. Nevertheless, this data can be received and processed at the instrument management system 5.

It will be discussed below in connection with FIG. 4 that the data processing module 2 can also be employed to transmit data from the instrument management system 5 to the analytical instrument(s) 1a, 1b. However, several aspects of the encryption methods that can be employed in the techniques of the present disclosure will be discussed first.

Aspects of Encryption and Decryption Techniques

As discussed above, in general any encryption technique can be used to provide the first and second encryption 7, 8 to the instrument data 3 and/or metadata 4.

In one example, applying the first encryption 7 to the instrument data 3 can include using a first encryption key and applying the second encryption 8 to the metadata 4 can include using a second encryption key different from the first encryption key. In some examples, the first encryption key can be a customer specific key of an operator of the analytical instrument 1a, 1b and the second key can be a vendor specific key of a vendor of the analytical instrument 1a, 1b. However, in other examples, the second key can be a key of a third party providing services by processing metadata 4 generated from instrument data 3. In general, the second key can be a key of any party operating the remote server 9 through which the encrypted data shall be sent.

The keys used for the first/second encryption can be public keys of a public key encryption scheme. In other examples, the keys used for the first/second encryption can be private keys of a private key encryption scheme.

In one example, the first encryption key can be a first public key of a first, client-specific asymmetric encryption key pair. In addition, or alternatively, the second encryption key can be a second public key of a second, vendor-specific asymmetric encryption key pair. Again, the "client" can be any entity described herein operating the analytical instrument 1a, 1b. Likewise, the "vendor" can be any entity operating the remote server 9.

In this example, removing the second encryption 8 from the metadata 4 at the remote server 9 can comprise decrypting the metadata 4 using a second private key of the second asymmetric encryption key pair and/or removing the first encryption 7 from the received instrument data 3 at the management system 5 can comprise decrypting the metadata 4 using a first private key of the first asymmetric encryption key pair.

As discussed above, the data processing module 2 can apply the first and second encryption 7, 8 to the data received from the analytical instrument 1a, 1b. If this encryption uses keys, these keys can be managed in different ways.

In one example, the data processing module 2 can be configured to only temporarily store a first encryption key or a second encryption key. For example, the data processing module 2 can be configured to retrieve the first encryption key prior to applying the first encryption 7 and delete the first encryption key after applying the first encryption 7. In this manner, the first encryption key does not have to be permanently stored on the data processing module 2a, 2b.

In other examples, the data processing module 2a can be configured to receive a second key for the second encryption 8 (e.g., a vendor key) from the remote server 9. For example, the second key can be a dynamic key that is used only for a predetermined period of time or for a specific purpose. In one example, the second key can be a temporary session key or a key only used for a single message.

However, in some examples the data processing module 2 can also be configured to permanently store the first and/or second keys used in the different encryption steps.

In some examples, the second key can be a key of the operator of the remote server 9 which can be specific for the operator of the analytical instrument 1a, 1b (e.g., the client).

In the present disclosure, the first and second encryption 7, 8 of the instrument data 3 and/or metadata 4 is discussed. In some examples, different additional encryption layers can be applied at different stages of the data transmission process. For example, a message sent from a data processing module 2a to a remote server 9 via the internet can be encrypted with an additional layer of encryption in some examples.

After different aspects of the communication of instrument data through the data processing module 2a, 2b have been discussed in general in connection with FIG. 1 and FIG. 2, further aspects of the techniques of the present disclosure will be explained in the context of two examples shown in FIG. 3 and FIG. 4.

Figure 3:
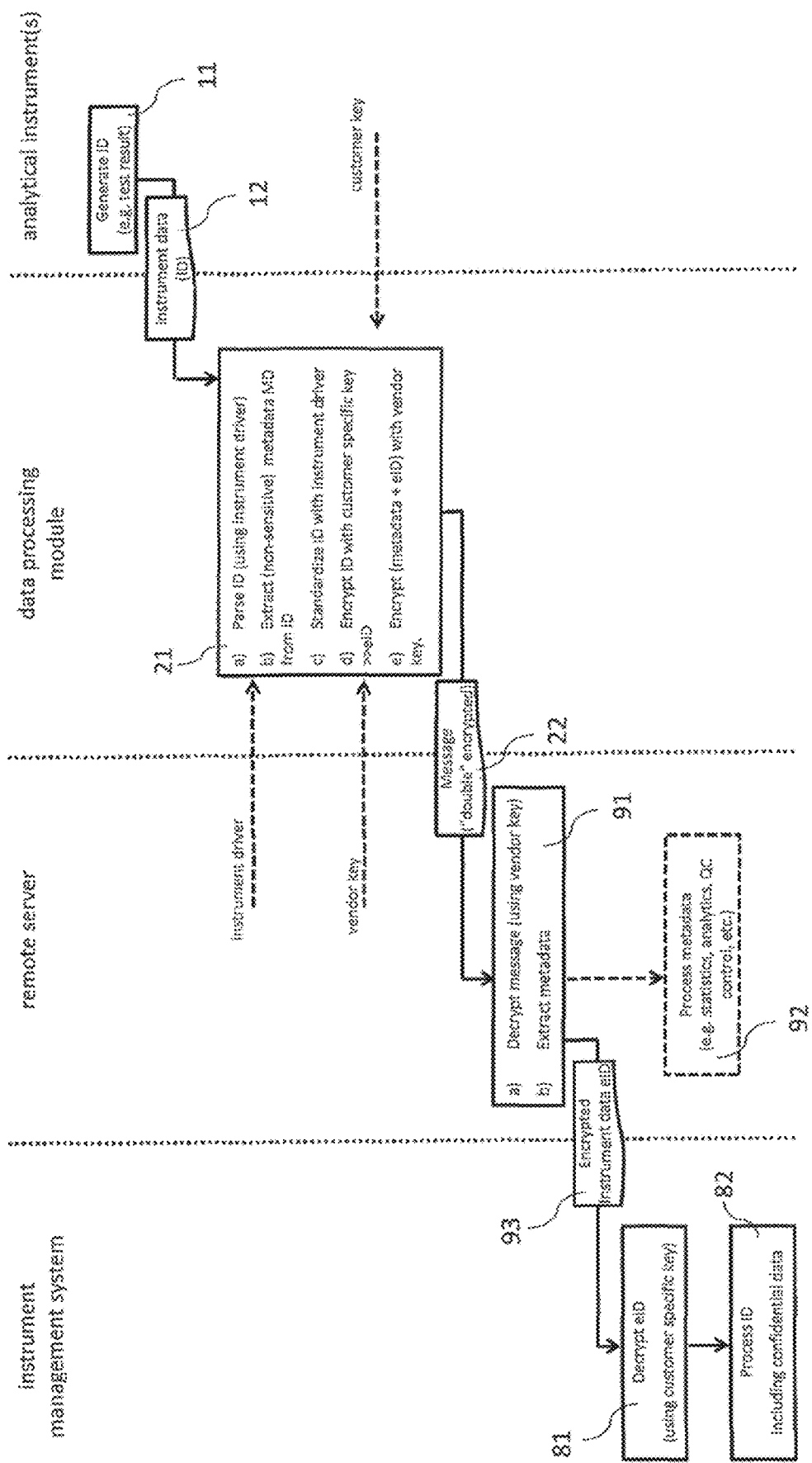
FIG. 3 illustrates a swim-lane diagram of a method of transmitting data from an analytical instrument to an instrument management system according to an embodiment of the present disclosure.

Transmitting Data from an Analytical Instrument to an Instrument Management System FIG. 3 illustrates a swim-lane diagram illustrating a method of transmitting data 3 from an analytical instrument 1a, 1b to an instrument management system 5 according to the present disclosure.

As discussed above, the process can start with an analytical instrument generating 11 instrument data ("ID"). For instance, the instrument data might include a test result of an in-vitro assay and patient and billing data associated with the test result and the assay.

In a next step, the instrument data can be transferred 12 to the data processing module. The data processing module can then process 21 the instrument data. As described above, this can include generating metadata 4. In FIG. 3, the generating process of the metadata can include extracting all non-sensitive data from the instrument data 3. In the example above, this can include the test result of an in-vitro assay but not the patient and billing data associated with the test result and the assay.

The processing can also include encrypting the instrument data and metadata with first and second encryption levels. In the example of FIG. 3, encrypting the data can include using a vendor key from the remote server and a customer key received from the analytical instrument. In addition, in the example of FIG. 3, the instrument data can be encrypted doubly by using first (customer) and second (vendor) keys. However, any other encryption technique described in the present disclosure can also be employed.

In addition to the steps of generating the metadata and the encryption steps, the data processing module can also parse the instrument data. This process will be discussed next.

In general, the parsing process can include receiving the instrument data in a first instrument format and identifying the data items contained in the instrument format data. In some examples, the data processing module can use one or more instrument drivers in the parsing process. The instrument drivers can be provided by the remote server in some examples.

One reason for the parsing step can be that instrument data in a format as received from the analytical instrument might be ill-suited or not suited for further processing. In particular, the generation process of the metadata (e.g., the identification process of sensitive and non-sensitive data) might require the parsing process in some examples.

A reason for this may be that many analytical instruments can have legacy control systems which can output instrument data in legacy and/or proprietary formats. These formats might not be digestible by later generation devices or management systems. As a consequence, it might be difficult to identify the information contained in the instrument data (e.g., to decide if it is sensitive or not-sensitive information).

For instance, an analytical instrument might output the result of the in-vitro assay and the patient and billing data associated with the test result and the assay mentioned above as a single string of characters. In this example, the parsing process can include identifying which data items are contained in the string.

In one example, the parsing process can include transforming the instrument data in a second format for further processing or transmission. Again, instrument drivers can be used in this process.

In some examples, the transformation process can include standardizing the instrument data by using an instrument driver. The data processing module can transform the instrument data into a data format specified at the instrument management system of an entity operating the analytical instrument. However, the data processing module can also transform the instrument data into any other standardized data format (e.g., an industry standard for data produced by a particular analytical instrument).

In a further step 22, the encrypted (and possibly standardized) data can be transmitted to the remote server. In one example, the remote server can be a server of the vendor of the analytical instrument. As highlighted in FIG. 3, the instrument data can be encrypted by the first encryption and the instrument data and the metadata can be encrypted by the second encryption. In other examples, any other encryption technique describe above can be employed.

Possible operations that take place at the remote server will be discussed next. As discussed above, the remote server can be operated by any third party. However, in the present example, the remote server might be a remote server of a vendor of the analytical instrument for the sake of illustration.

At the remote server, the received data can be prepared for further processing 91. In a first step, the second encryption can be removed (e.g., by using a vendor key). As a result, the metadata can be accessible. In the example of FIG. 3, the metadata can be extracted at the remote server.

The so extracted metadata can subsequently be processed 92 in different ways at the remote server. Several example processing operations will be discussed in the subsequent sections.

In one example, one or more analytical operations can be applied on the metadata. In this manner, analysis data regarding one or more patients can be generated. For example, the analysis data can include information related to a test result of a particular assay (or a plurality of test results) contained in the metadata.

In addition, or alternatively, the processing at the remote server can include performing statistics on the metadata received from one or more analytical instruments. For instance, statistics for a plurality of test result or measurement results of one or more analytical instruments can be calculated.

In other examples, the processing of the metadata can yield data used for monitoring of the analytical instrument. For, instance the measurement data included in the metadata can be helpful to assess a state of the analytical instrument (or of a component of the analytical instrument). In one illustrative example, the metadata can reveal that an illumination unit of the analytical instrument has a low light output. This can be interpreted as an indication of a near end-of-life of the illumination unit. In the same manner, the state of other components can be assessed.

In another example, the metadata can be used to for quality control purposes. For many analytical instruments, it can be required to perform quality control measurement at predetermined points in time to assess if the analytical instrument is operating properly. The results of these measurements can be included in the metadata and processed at the remote server.

The data obtained at the remote server by processing the metadata can be transmitted to the instrument management system in some examples (not shown in FIG. 3). In addition, or alternatively, the data generated at the remote server by processing the metadata can be transmitted to the analytical instrument in some examples (also not shown in FIG. 3).

Regardless of the nature of the analytical operations, the encrypted (by the first encryption) instrument data can be forwarded to the instrument management system.

At the data management system, the first encryption can be removed from the instrument data (e.g., including sensitive data). The instrument data can then be processed in any suitable manner.

As can be seen in the example of FIG. 3, the technique of the present disclosure including using a data processing module as described herein can allow connecting analytical instruments (including legacy instruments) to a network for data transmission to a (central) data management system. Moreover, the technique can allow including third parties in the transmission loop. At the same time, sensitive data can be protected from access by non-entitled parties.

Transmitting Data from an Instrument Management System to an Analytical Instrument In the preceding sections, the technique of the present disclosure has been described for transmitting instrument data to a data management system 5. However, the techniques of the present disclosure can also be used to transfer data in the opposite direction, i.e., from the data management system 5 to an analytical instrument 1*a*, 1*b*. Aspects of this technique will be discussed in the following paragraphs in connection with FIG. 4.

Figure 4:
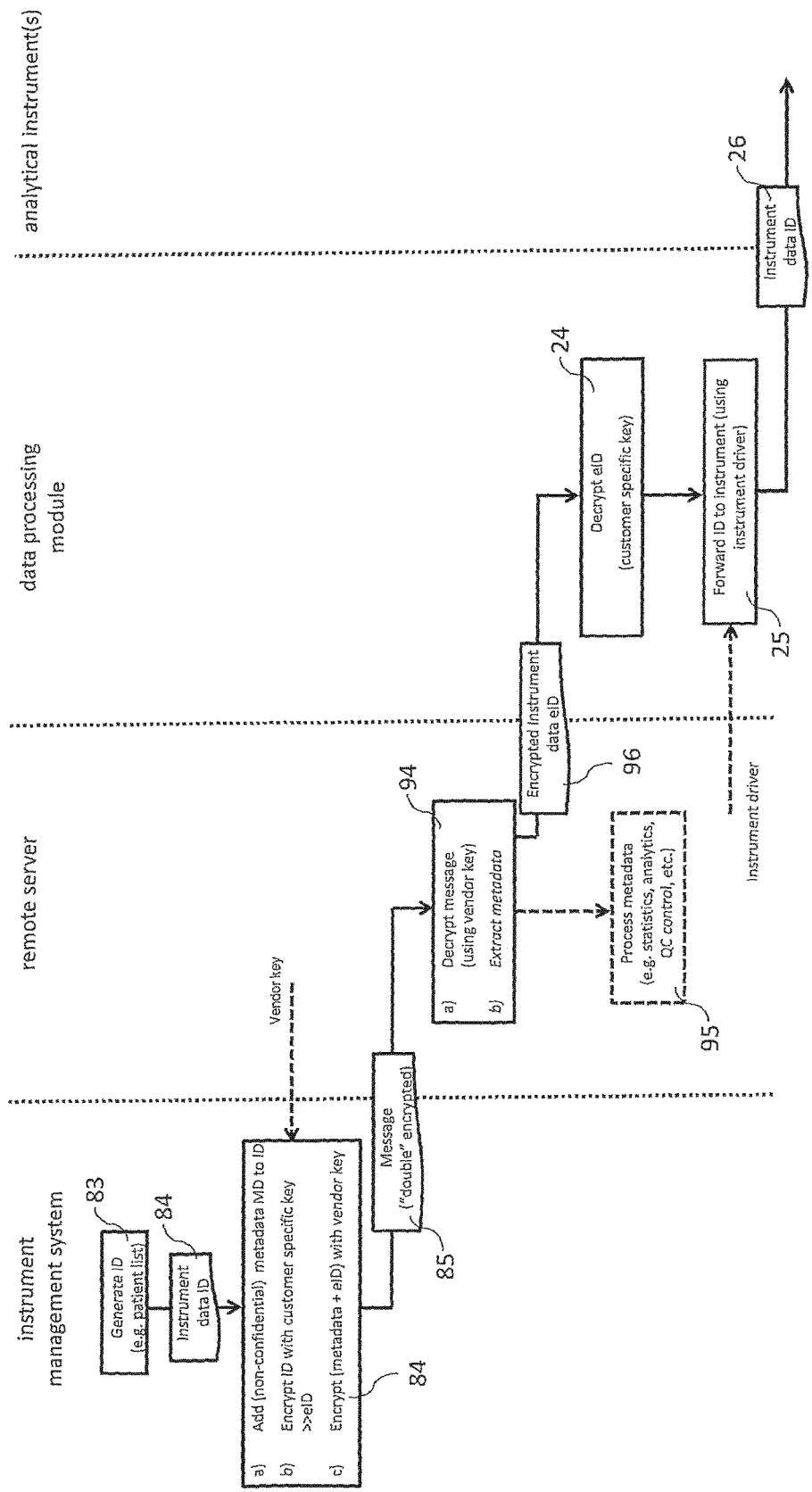
FIG. 4 illustrates swim-lane diagram of a method of transmitting data from an instrument management system to an analytical instrument according to an embodiment of the present disclosure.

FIG. 4 illustrates a swim-lane diagram illustrating a method of transmitting data from an instrument management system 5 to an analytical instrument 1*a*, 1*b* to according to the present disclosure.

In a first step 83, instrument data can be generated at the instrument management system (instrument data generated at the instrument management system is also referred to as "input data" in the present disclosure). In general, the instrument data can include any data which can be present at the instrument management system and can be transmitted to the analytical instrument.

For example, the instrument data can include a patient list (e.g., a list of patients for who tests can be performed with the analytical instrument). In other examples, the instrument data can include an order list of tests or assays to be carried out at the analytical instrument. In general, the instrument data can include patient- or client-specific information (i.e., sensitive data).

In a further step 84, the instrument data can be processed at the data management system. This processing can include generating metadata and applying a first and second encryption. These steps can include any of the aspects described in connection with the generation of metadata and first and second encryption steps of instrument data originating from the analytical instrument discussed above. Naturally, the nature of the instrument data and metadata can be different in some examples to the instrument management system side.

In some examples, the generating process of the metadata and the encryption can be performed by data processing module as described herein. On the instrument management side, the data processing module can be a software module (e.g., a SaaS module).

In any case, the data processing module can generate a double encrypted message. This message can be transmitted to the remote server in a further step 85. At the remote server, the received message can be processed. The processing steps 94-96 can include the same processing steps as described above in connection with FIG. 3 (unless the respective processing step only makes sense in connection with data received from the analytical instrument and not in connection with data received from the data management system).

The processing can include removing the second encryption and extracting the metadata contained in the message. Subsequently, the processed data can be forwarded 96 to a data processing module.

The data processing module can further process the received data. This can involve decrypting the received data to remove the first level of encryption. In addition, the data processing module can bring the data into a format suitable to be processed by the analytical instrument. As discussed above when discussing the "other transmission direction," this can involve using instrument drivers stored at the data processing module—In some examples, the instrument drivers can be received from the remote server at the data processing module. In this manner, the instrument data can be transformed into a format digestible by the analytical instrument (e.g., a legacy data format used by a controller of the analytical instrument).

In a further step 26, the data processing module can transmit the decrypted (and possibly reformatted) data to the analytical instrument. At the analytical instrument, the data can be used in different ways to facilitate the operation of the analytical instrument.

Similar to the example process for transmitting data from the analytical instrument to the instrument management system in a secure manner described in connection with FIG. 3 above, the data processing modules can also allow for a secure transmission of instrument data in the opposite direction. As can be seen, an operator of the analytical instruments and the instrument management system do not have to change or update the software or firmware of the respective devices to facilitate this secure communication. It can be sufficient to employ one or more data processing modules which can enable the secure communication.

In particular, legacy instruments or instruments distributed widely over different locations (e.g., patients' homes) can be connected by using this technique. In addition, smaller entities such as doctors' offices can network their analytical instruments and instrument management systems in a relatively straightforward manner.

Moreover, the data processing modules can allow third parties to be included in the transmission loop which can allow providing additional services to the operator of the analytical instrument and the instrument management system.

In the preceding detailed description, multiple examples of methods and systems for processing data of an analytical instrument for analyzing biological samples have been discussed. However, the methods and systems for processing data of an analytical instrument for analyzing biological samples can also be configured as set out in the following:

A method for processing data of an analytical instrument for analyzing biological samples is presented. The method can comprise receiving instrument data from the analytical instrument at a data processing module communicatively connected with the analytical instrument, generating metadata from the received instrument data at the data processing module, applying a first encryption to the instrument data at the data processing module, applying a second encryption to the generated metadata at the data processing module, and transmitting the encrypted metadata and encrypted instrument data to a remote server. The remote server and the data processing module can be communicatively connected. The method can also comprise removing the second encryption from the metadata at the remote server, and forwarding the instrument data encrypted by the first encryption from the remote server to a management system of the analytical instrument.

The applying the first encryption comprises using a first encryption key and applying the second encryption comprises using a second encryption key can different from the first encryption key. The one first encryption key can be a customer specific key of a user of the analytical instrument. The second key can be a vendor specific key of a vendor of the analytical instrument.

The method can further comprise retrieving the first encryption key prior to applying the first encryption at the data processing module and deleting the first encryption key after applying the first encryption.

The generating metadata can comprise parsing the instrument data received from the analytical instrument by using one or more drivers specific to the analytical instrument stored at the data processing module.

The method can further comprise receiving the one or more drivers from the remote server.

The generating the metadata can comprise removal of patient-specific data and/or client-specific data from the instrument data received from the analytical instrument.

The method can further comprise extracting the metadata at the remote server and processing the metadata at the remote server by performing one or more analytical operations.

The method can further comprise receiving the instrument data at the management system of the analytical instrument, removing the first encryption from the received instrument data at the management system, and processing the instrument data at the management system including patient-specific data.

The first encryption key can be a first public key of a first customer specific asymmetric encryption key pair and/or the second encryption key can be a second public key of a second vendor specific asymmetric encryption key pair.

The removing the second encryption from the metadata at the remote server can comprise decrypting the metadata using a second private key of the second asymmetric encryption key pair and/or removing the first encryption from the received instrument data at the management system can comprise decrypting the metadata using a first private key of the first asymmetric encryption key pair.

The second encryption can also be applied to the instrument data at the data processing module.

A method for processing data of a management system of analytical instruments can comprise receiving input data at the management system of analytical instruments, generating metadata based on the input data at the management system of analytical instruments, applying a first encryption to the input data at the management system, applying a second encryption to the generated metadata at the management system, and transmitting the encrypted data from the management system to a remote server. The remote server and the management system can be communicatively connected. The method can also comprise removing the second encryption from the data at the remote server, transmitting the input data to a data processing module communicatively connected to an analytical instrument for analyzing biological samples, removing the first encryption from the input data at the data processing module, and forwarding the input data from the data processing module to the analytical instrument.

The applying the first encryption can include using a first encryption key and applying the second encryption can include using a second encryption key different from the first encryption key. The one first encryption key can be a customer specific key of a user of the analytical instrument and the second key can be a vendor specific key of a vendor of the analytical instrument.

The method can further comprise retrieving the first encryption key prior to removing the first encryption from the input data at the data processing module and deleting the first encryption key after removing the first encryption.

The forwarding the input data to the analytical instrument for analyzing biological samples can include using one or more drivers specific to the analytical instrument stored at the data processing module.

The method can further comprise receiving the one or more drivers from the remote server.

The method can further comprise extracting the metadata at the remote server and processing the metadata at the remote server by performing one or more analytical operations.

The method can further comprise receiving the input data at the analytical instrument for analyzing biological samples and processing the input data at the analytical instrument for analyzing biological samples.

The first encryption key can be a first public key of a first customer specific asymmetric encryption key pair and/or the second encryption key can be a second public key of a second vendor specific asymmetric encryption key pair. Removing the second encryption from the metadata at the remote server can comprise decrypting the metadata using a second private key of the second asymmetric encryption key pair and/or removing the first encryption from the received instrument data at the management system can comprise decrypting the metadata using a first private key of the first asymmetric encryption key pair.

The second encryption can also be applied to the input data at the data processing module.

The data processing module can be a hardware module.

The hardware module can be a stand-alone hardware module. The hardware module can include a dedicated power supply configured to power the data processing module. The power supply can include one or more batteries. The power supply can include one or more capacitors, or both.

The data processing module can be run as a platform as a service or infrastructure as a service. The data processing module can provide capabilities to connect the analytical instrument to a communication network. The communication network can be a wireless communication network.

A system for processing data of an analytical instrument for analyzing biological samples is presented. The system can comprise a data processing module communicatively connected with the analytical instrument configured to receive instrument data from an analytical instrument for analyzing biological samples, generate metadata from the received instrument data, apply a first encryption to the instrument data but not the metadata, apply a second encryption to the generated metadata, and transmit the encrypted metadata and encrypted instrument data to a remote server.

The system can further comprise a remote server configured to remove the second encryption from the metadata at the remote server and forward the instrument data encrypted by the first encryption to a management system of the analytical instrument for analyzing biological samples.

The system can further comprise the analytical instrument and/or the management system of the analytical instrument for analyzing biological samples.

The system can be further configured to carry out the above methods.

A system for processing data of a management system for analytical instruments of analytical instruments can comprise a management system for analytical instruments configured to receive input data, generate metadata based on the input data, apply a first encryption to the input data, apply a second encryption to the generated metadata, and transmit the encrypted data to a remote server; a remote server configured to remove the second encryption from the data and transmit the input data to a data processing module communicatively connected to an analytical instrument for analyzing biological samples; and a data processing module communicatively connected to an analytical instrument for analyzing biological samples configured to remove the first encryption from the input data and forward the input data to the analytical instrument for analyzing biological samples.

The system can be further configured to carry out the above methods.

The data processing module can be a hardware module. The hardware module can be a stand-alone hardware module. The hardware module can include a dedicated power supply configured to power the data processing module. The power supply can include one or more batteries or the power supply can include one or more capacitors, or both.

The data processing module can be run as a platform as a service or infrastructure as a service. The data processing module can provide capabilities to connect the analytical instrument to a communication network. The communication network can be a wireless communication network.

A computer-readable medium storing instructions thereon which when executed by a computer system can make the computer system perform the above methods 1.

Computer-Implementation

Further disclosed and proposed is a computer program including computer-executable instructions for performing the method according to the present disclosure in one or more of the embodiments enclosed herein when the program can be executed on a computer or computer network. Specifically, the computer program may be stored on a computer-readable data carrier. Thus, specifically, one, more than one or even all of method steps as disclosed herein may be performed by using a computer or a computer network, preferably by using a computer program.

Further disclosed and proposed is a computer program product having program code, in order to perform the method according to the present disclosure in one or more of the embodiments enclosed herein when the program can be executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product can refer to the program as a tradable product. The product may generally exist in an arbitrary format, such as in a paper format, or on a computer-readable data carrier. Specifically, the computer program product may be distributed over a data network.

Further disclosed and proposed is a modulated data signal which can contain instructions readable by a computer system or computer network, for performing the method according to one or more of the embodiments disclosed herein.

Referring to the computer-implemented aspects of the present disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer, or computer network, comprising at least one processor, wherein the processor can be adapted to perform the method according to one of the embodiments described in this description.

Further disclosed and proposed is a computer loadable data structure that can be adapted to perform the method according to one of the embodiments described in this description while the data structure is being executed on a computer.

Further disclosed and proposed is a storage medium, wherein a data structure can be stored on the storage medium and wherein the data structure can be adapted to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critic al, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A computer-implemented method for processing data from one or more analytical instruments for analyzing biological samples, the computer-implemented method comprising:
   receiving, by a data processing module communicatively connected with the one or more analytical instruments, instrument data from the one or more analytical instruments;
   generating, by the data processing module, metadata based on at least one of the instrument data or further data;
   generating, by the data processing module, encrypted instrument data by applying a first encryption to the instrument data;
   generating, by the data processing module, encrypted metadata by applying a second encryption to the metadata; and
   transmitting, by the data processing module, the encrypted metadata and the encrypted instrument data to a remote server that is configured to:
      access the metadata by removing the second encryption from the encrypted metadata,
      determine, by processing the metadata, at least one operating state of the one or more analytical instruments, and
      forward the encrypted instrument data to a remote data processing system different from the data processing module.

2. The computer-implemented method of claim 1, wherein:
   applying the first encryption comprises using a first encryption key to encrypt the instrument data, and
   applying the second encryption comprises using a second encryption key, different from the first encryption key, to encrypt the metadata.

3. The computer-implemented method of claim 1, wherein the one or more analytical instruments comprise one or more of: clinical chemistry analyzers, coagulation chemistry analyzers, immunochemistry analyzers, hematology analyzers, urine analyzers, or nucleic acid analyzers.

4. The computer-implemented method of claim 1 wherein the one or more analytical instruments comprise at least one automated analyzer.

5. The computer-implemented method of claim 1, wherein the metadata omits billing data.

6. The computer-implemented method of claim 1, wherein:
   the instrument data comprises private patient data, and
   the metadata omits the private patient data.

7. The computer-implemented method of claim 1, further comprising:
   applying, by the data processing module, the second encryption to the encrypted instrument data that is encrypted with the first encryption,
   wherein the remote server is configured to remove the second encryption from the encrypted instrument data prior to forwarding the encrypted instrument data, still encrypted with the first encryption, to the remote data processing system.

8. The computer-implemented method of claim 1, wherein the remote data processing system is configured to:

receive the encrypted instrument data from the remote server;

access the instrument data by removing the first encryption from the encrypted instrument data; and process the instrument data.

9. The computer-implemented method of claim 1, further comprising:

transforming, by the data processing module, the instrument data from a first format into a second format for at least one of further processing or transmission, wherein the second format is compatible with the remote data processing system.

10. A computing system configured to process data from one or more analytical instruments for analyzing biological samples, the computing system comprising:

one or more processors; and memory storing computer-executable instructions for a data processing module that, when executed by the one or more processors, cause the computing system to:

receive instrument data from the one or more analytical instruments;

generate metadata based on at least one of the instrument data or further data, generate encrypted instrument data by applying a first encryption to the instrument data, generate encrypted metadata by applying a second encryption to the metadata; and transmit the encrypted metadata and the encrypted instrument data to a remote server that is configured to:

access the metadata by removing the second encryption from the encrypted metadata, determine, by processing the metadata, at least one operating state of the one or more analytical instruments, and forward the encrypted instrument data to a remote data processing system different from the computing system that executes the data processing module.

11. The computing system of claim 10, wherein;

applying the first encryption comprises using a first encryption key to encrypt the instrument data, and applying the second encryption comprises using a second encryption key, different from the first encryption key, to encrypt the metadata.

12. The computing system of claim 10, wherein the one or more analytical instruments comprise one or more of clinical chemistry analyzers, coagulation chemistry analyzers, immunochemistry analyzers, hematology analyzers, urine analyzers, or nucleic acid analyzers.

13. The computing system of claim 10, wherein the one or more analytical instruments comprise at least one automated analyzer.

14. The computing system of claim 10, wherein the remote data processing system is configured to:

receive the encrypted instrument data from the remote server;

access the instrument data by removing the first encryption from the encrypted instrument data; and process the instrument data using at least one data analysis operation.

15. The computing system of claim 10, wherein:

the instrument data comprises private patient data, and the metadata omits the private patient data.

16. The computing system of claim 10, wherein the metadata omits billing data.

17. The computing system of claim 10, wherein:

the computer-executable instructions further cause the computing system to apply the second encryption to the encrypted instrument data that is encrypted with the first encryption, and the remote server is configured to remove the second encryption from the encrypted instrument data prior to forwarding the encrypted instrument data, still encrypted with the first encryption, to the remote data processing system.

18. The computing system of claim 10, wherein:

the computer-executable instructions further cause the computing system to transform the instrument data from a first format into a second format for at least one of further processing or transmission, and the second format is compatible with the remote data processing system.

19. The computer-implemented method of claim 1, wherein the remote server is associated with at least one of:

an operator of the one or more analytical instruments, or a vendor of the one or more analytical instruments.

20. The computer-implemented method of claim 1, wherein the at least one operating state of the one or more analytical instruments, determined by the remote server by processing the metadata, indicates at least one of:

quality control information associated with the one or more analytical instruments, or states of one or more components of the one or more analytical instruments.

* * * * *